US011027144B2

(12) United States Patent
Angel et al.

(10) Patent No.: US 11,027,144 B2
(45) Date of Patent: *Jun. 8, 2021

(54) LASER THERAPY FOR AT LEAST ONE OF GRADE III AND GRADE IV CAPSULAR CONTRACTURE

(71) Applicant: Riancorp Pty Ltd, Richmond (AU)

(72) Inventors: Patricia Ann Angel, Henley Beach (AU); William L. Scarlett, Holland, PA (US)

(73) Assignee: Riancorp Pty Ltd, Richmond (AU)

(*) Notice: Subject to any disclaimer, the term of this patent is extended or adjusted under 35 U.S.C. 154(b) by 170 days.

This patent is subject to a terminal disclaimer.

(21) Appl. No.: 15/795,231

(22) Filed: Oct. 26, 2017

(65) Prior Publication Data
US 2018/0110998 A1   Apr. 26, 2018

Related U.S. Application Data

(63) Continuation of application No. 14/598,467, filed on Jan. 16, 2015, now Pat. No. 9,808,645.

(60) Provisional application No. 61/928,623, filed on Jan. 17, 2014.

(51) Int. Cl.
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0659* (2013.01)

(58) Field of Classification Search
CPC ............ A61N 5/0613; A61N 2005/067; A61N 2005/0659; A61N 2005/0662
See application file for complete search history.

(56) References Cited

U.S. PATENT DOCUMENTS

| 6,022,317 A | 2/2000 | Cruanas et al. |
| 6,060,474 A | 5/2000 | Williams et al. |
| 6,951,869 B2 | 10/2005 | Schlesinger |
| 2003/0171795 A1 | 9/2003 | Walmsley et al. |
| 2009/0132012 A1 | 5/2009 | Shanks |
| 2010/0234772 A1 | 9/2010 | Weyant |
| 2015/0202458 A1 | 7/2015 | Angel et al. |

FOREIGN PATENT DOCUMENTS

RU   2129029   4/1999

OTHER PUBLICATIONS

Johnson, J. D., Glat, P. M., & Scarlett, W. L. Low-Level Laser Therapy: An Alternative Treatment for Capsular Contraction. The American Journal of Cosmetic Surgery, 32(1), 7-11. https://doi.org/10.5992/AJCS-D-14-00036.1 (Year: 2015).*

(Continued)

*Primary Examiner* — Nathan J Jenness
(74) *Attorney, Agent, or Firm* — Martin IP Pty Ltd

(57) ABSTRACT

A method for treating at least one of Grade III capsular contracture and Grade IV capsular contracture in a mammalian subject includes positioning a laser device proximate to the subject. The method also includes applying low level near infrared radiation to an area of the subject proximate to tissue in the subject experiencing at least one of Grade III capsular contracture and Grade IV capsular contracture for treating the capsular contracture.

14 Claims, 5 Drawing Sheets

(56) References Cited

OTHER PUBLICATIONS

Farhad Azimi; Kathy Flitcroft; Erin Mathieu; Rebecca Karantonis; Kylie Snook; Andrew Spillane. Low-Level Laser Treatment Is Ineffective for Capsular Contracture: Results of the LaTCon Randomized Controlled Trial. Plastic and Reconstructive Surgery. 142(5):621e-631e (Year: 2018).*
Jackson et al., Low-Level Laser Therapy Effectiveness for Reducing Pain After Breast Augmentations, American Journal of Cosmetic Surgery, vol. 265, No. 3, pp. 1-6, 2009.
Horvath et al., Possible ab-inito explanation of laser biostimulation effects, Laser Applications in Medicine and Surgery, pp. 57-60, Sep. 1992.
Lamuraglia et al., Photodynamic application on arteries, Laser Applications in Medicine and Surgery, pp. 439-444, Sep. 1992.
Glassberg et al., Cellular Effects of the Pulsed Tunable Dye Laser at 577 Nanometers on Human Endothelial Cells, Firbroblasts, and Erythrocytes: An In Vitro Study, Lasers in Surgery and Medicine, vol. 8, pp. 567-572, 1988.
Tadakuma, Possible Application of the Laser in Immunobiology, Special Lecture Session, Keio Journal of Medicine, vol. 42, pp. 180-182, 1993.
Young et al., Macrophage Responsiveness to Light Therapy, Lasers in Surgery and Medicine, vol. 9, pp. 497-505, 1989.
Karu, Photobiological Fundamentals of Low-Power Laser Therapy, Special Issue Papers, IEEE Journal of Quantum Electronics, vol. QE-23, No. 10, Oct. 1987, pp. 1703-1717.
Karu, Photobiology of Low-Power Laser Effects, Health Physics, vol. 56, No. 5, pp. 691-706, 1989.
Boulton et al., He—Ne Laser Stimulation of Human Fibroblast Proliferation and Attachment in Vitro, Lasers in the Life Sciences, vol. 1, pp. 125-134, 1986.
Inoue et al., Altered lymphocyte proliferation by low dosage laser irradiation, Clinical and Experimental Rheumatology, vol. 7, pp. 521-523, 1989.
Lievens, The Effect of a Combined HeNe and I.R. Laser Treatment on the Regeneration of the Lymphatic System During the Process of Wound Healing, Lasers in Medical Sciences, vol. 6, pp. 193-199, 1991.
Lievens, P., The influence of Laser-irradiation on the motricity of lymphatical system and on the wound healing process, International Congress on Laser in Medicine and Surgery, Bologna, Jun. 26-28, 1985, pp. 171-174.
Non-Final Rejection in U.S. Appl. No. 13/442,441, dated May 2, 2013.
Response to Non-Final Rejection in U.S. Appl. No. 13/442,441, dated Aug. 2, 2013.
Final Rejection in U.S. Appl. No. 13/442,441 dated Aug. 29, 2013.

* cited by examiner

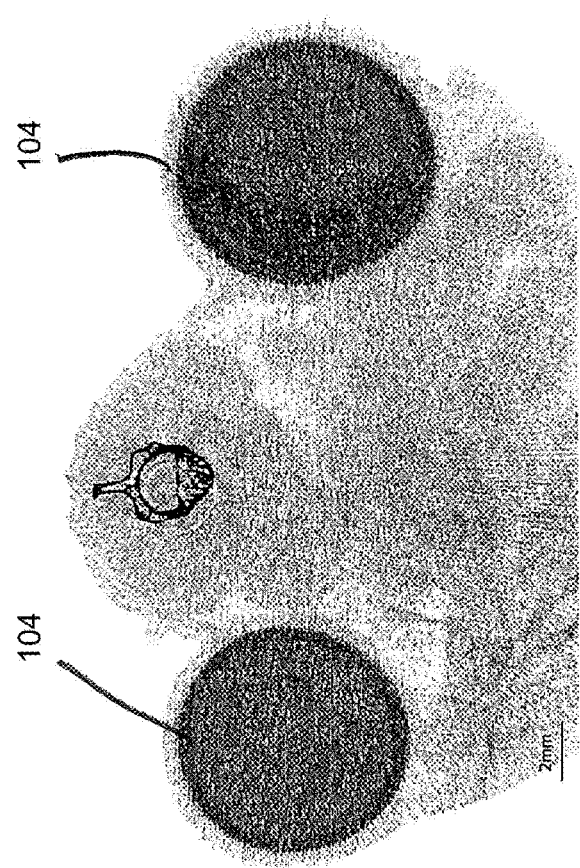

| n | Is your breast more comfortable post-LLLT? | If so, by what percentage? | Is your breast softer post-LLLT? | If so, by what percentage? | Would you try LLLT again to try to further soften your breast? | Is your breast improved enough to avoid having corrective surgery? |
|---|---|---|---|---|---|---|
| 1 | Yes | 25-30% | Yes | 25-30% | Yes | Yes |
| 2 | Yes | 40-50% | Yes | 30% | Yes | Yes |
| 3 | No | --- | No | --- | No | No |
| 4 | Yes | 25-30% | Yes | 25-30% | Yes | Yes |
| 5 | Yes | 90% | Yes | 90% | Yes | Yes |
| 6 | No | --- | No | --- | No | No |
| 7 | Yes | 50% | Yes | 50% | Yes | Yes |
| 8 | Yes | 40% | Yes | 40% | Yes | Yes |
| 9 | Yes | 25% | Yes | 25% | Yes | Yes |
| 10 | Yes | 95% | Yes | 95% | Yes | Yes |
| 11 | Yes | 10% | Yes | 10% | Yes | Yes |
| 12 | Yes | 50% | Yes | 50% | Yes | Yes |
| 13 | Yes | 60% | Yes | 60% | Yes | Yes |
| 14 | Yes | 30% | Yes | 30% | Yes | Yes |
| 15 | Yes | 50% | Yes | 30-40% | Yes | Yes |
| 16 | Yes | 50% | Yes | 60% | Yes | Yes |
| 17 | Yes | 40-50% | Yes | 40-50% | Yes | Yes |
| 18 | Yes | 80% | Yes | 80% | Yes | Yes |
| 19 | Yes | 75% | Yes | 65% | Yes | Yes |
| 20 | Yes | 25% | Yes | 25% | Yes | ?? |

FIG. 8

LASER THERAPY FOR AT LEAST ONE OF GRADE III AND GRADE IV CAPSULAR CONTRACTURE

CROSS-REFERENCE TO RELATED APPLICATION

This application claims priority to and all benefit of U.S. Provisional Patent Application Ser. No. 61/928,623, entitled "LASER THERAPY FOR AT LEAST ONE OF GRADE III AND GRADE IV CAPSULAR CONTRACTURE" and filed Jan. 17, 2014, the entire disclosure of which is incorporated herein by reference, to the extent that such disclosure does not conflict with the present application.

BACKGROUND

Implantation of prosthetic devices in mammals (e.g., breast implants used in cosmetic reconstruction of the breast) often result in contracture of a fibrotic capsule that develops around the prosthetic device. In the case of breast implants, this capsular contracture can result in hardness, discomfort, and deformation of the breast, often requiring further surgical intervention in more severe cases.

SUMMARY

The present invention relates to laser therapy. It finds particular application in conjunction with low level laser therapy (LLLT) for capsular contracture and will be described with particular reference to treating at least one of Grade III and Grade IV capsular contracture. It will be appreciated, however, that the invention is also amenable to other applications.

The present application describes new and improved methods for treating capsular contracture.

In one embodiment, a method for treating at least one of Grade III capsular contracture and Grade IV capsular contracture in a mammalian subject includes positioning a laser device proximate to the subject. The method also includes applying low level near infrared radiation to an area of subject proximate to tissue in the subject experiencing at least one of Grade III capsular contracture and the Grade IV capsular contracture for treating the capsular contracture.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

FIG. 3 illustrates implants in situ using 3D micro CT scanning;

FIG. 8 illustrates a chart of respective responses from the patients treated for capsular contracture in accordance with one embodiment illustrating principles of the present invention.

DETAILED DESCRIPTION

LLLT for Lymphedema

Figure 1:
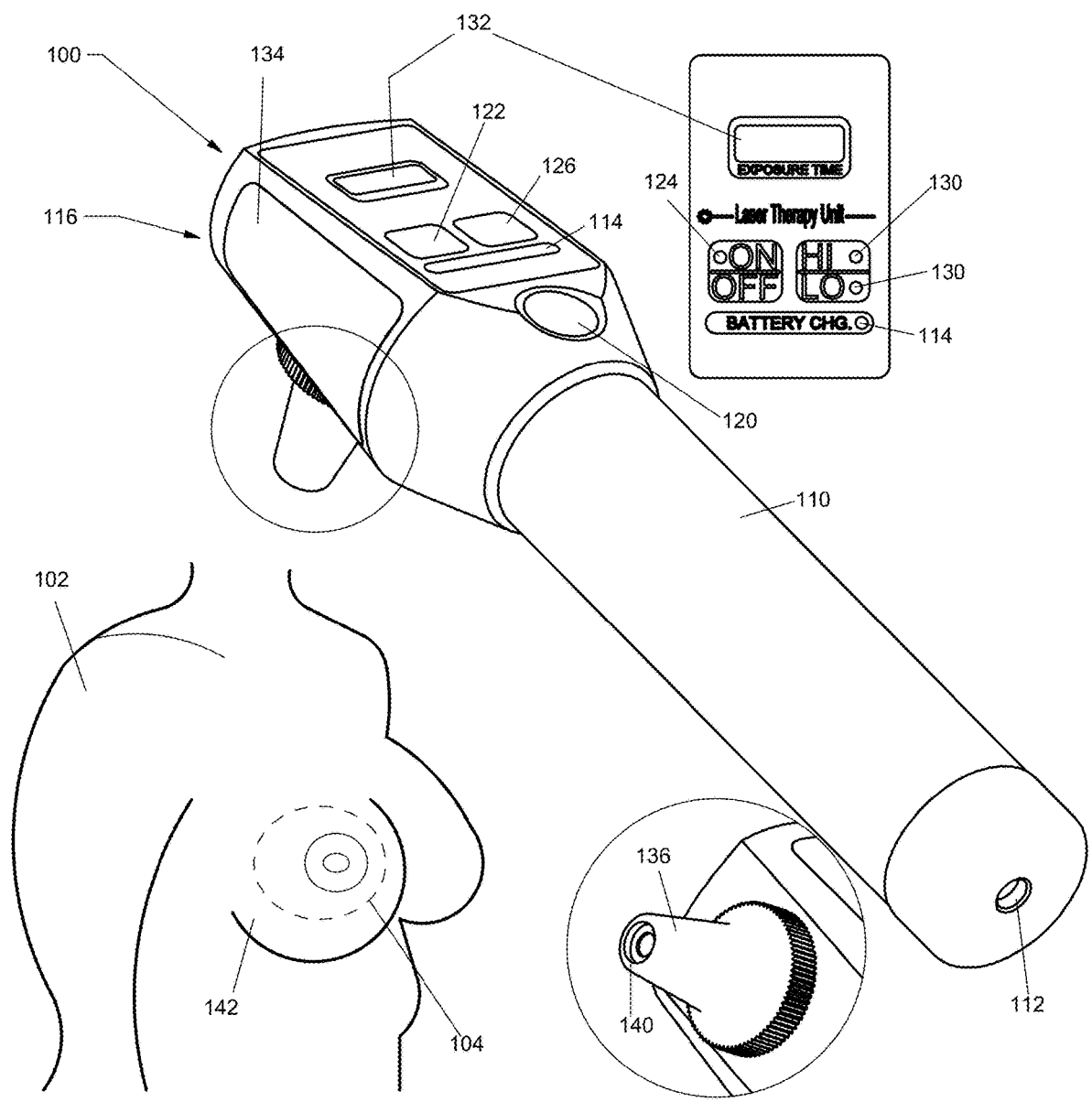
FIG. 1 illustrates a schematic representation of a laser device in accordance with one embodiment of an apparatus illustrating principles of the present invention.

LLLT is the application of low power levels (< about 1 Watt) of near infra-red or red light (about 600 nm-about 1100 nm) to the skin surface via a laser source. LLLT does not produce any discernible heat in the tissue. Therefore, the effects achieved are not thermal related, but, instead, are related to a photochemical reaction at a cellular level. This modality was first introduced in the 1960's in Hungary, Europe. Most applications have been used for pain relief or wound healing effects with many hundreds of clinical trials being published throughout the world. Since the 1960's, LLLT has been trialed and used for a range of conditions with varying degrees of success. Corresponding variations in the level of scientific evidence has also been a feature of this modality, however, evidence and applications have continued to be explored.

The US FDA cleared the first LLLT device for pain relief in 2001 and since that time, a number of devices have been cleared for treatment of a range of pain relief applications. A laser therapy device (e.g., the LTU-904) is offered for laser therapy and has been cleared for the treatment of post mastectomy lymphedema, which is a chronic swelling produced by excessive lymphatic fluid in the arm.

As discussed above, low level laser therapy (LLLT) is reported to have beneficial effects on cells and tissues and has been trialed for the treatment of fibrous scar tissue and has been shown to affect fibroblasts. These effects are important both in treating surgical scars associated with post-mastectomy lymphedema (PML) and in treating the brawny edema that often develops in lymphedematous limbs. There is also a suggestion that LLLT encourages lymphogenesis and stimulates lymphatic motricity. Finally, LLLT appears to affect macrophage cells and to stimulate the immune system.

Possible explanations for the beneficial effect of LLLT treatment for lymphedema include:

restoration of lymphatic drainage through the axillary region due to stimulation of new lymphatic pathways;
restoration of drainage through reduction of fibrosis and reduced scarring of tissues in the axillary region; and
reduction in tissue fluid accumulation through changes in blood flow, either directly via an effect of blood vessels or by neural regulation of vessels in the limb Theories on mechanism of action of LLLT in tissues.

Theories on the mechanism(s) of action of LLLT in tissues include interaction with the cytochromes of the mitochondrial electron transport chain, induction of local gradients in energy delivery due to laser speckle resulting in local gradients in cellular heating, stimulation of long term mitogenic activity, stimulatory/protective effects on fibroblasts and on lymphocytes, and stimulatory/protective effects on endothelial cells and vascular endothelium in situ. In addition, there are reports of stimulation of local fluid circulation, and stimulatory effects on lymphatic vessels.

The inventors have identified that patients with lymphedema, and also with a condition associated with breast implants known as "capsular contracture," who are treated with the LLLT (e.g., LTU-904 laser for lymphedema), reported considerable improvement in their capsular contracture symptoms.

Subsequent treatments over a 6 week period on a group of 10 patients resulted in significant sustained improvement in 100% of subjects.

Capsular Contracture

Capsular contracture is an identified condition where scar tissue around an implant (e.g., a breast implant) becomes tight and causes pain and distortion. The human body surrounds (i.e., encapsulates) at least some foreign objects, including, for example, a breast implant, in a fibrous substance (e.g., collagen) as a protective mechanism. If and when this capsule tightens (e.g., due to infection, radiation, trauma, or idiopathic conditions), constriction of the implant and physical distortion may result. Capsular contracture, capsule contracture, and capsular fibrosis are all terms used to describe a condition where the body's natural reaction to a foreign object (any implant) can result in excessive fibrous tissue being deposited around the foreign object. The result can be a range of complications. In breast implants, the implants can become distorted, painful, and/or displaced. Dental implants that have capsular fibrosis do not form appropriate fixture into the bone and must be removed and replaced. Intra-ocular lenses with excessive fibrosis can become distorted or moved. Lap bands, designed to be adjustable, cannot be adjusted, if there is excessive fibrotic contracture. Cochlear hearing implants can also be effected by excessive fibrotic contracture. Fibrotic contracture can affect any implant and lead to complications such as pain, distortion or inappropriate movement of the implant.

It has been reported that up to 25% of breast implants may be affected by capsular constriction to various degrees. Approximately 10% of breast augmentation patients report significant capsular contracture. This can be a significant complication from breast implant surgery, both reconstructive and cosmetic. Surgeons grade the severity of capsular contracture into 4 grades known as the Baker Scale:

Grade I: is when the breast looks natural and is soft to touch;
Grade II: the breast looks normal but is a little firm to touch;
Grade III: is characterized by the abnormal look of the breast and it is firm to touch; and
Grade IV: the breast looks abnormal and is hard and painful.

The typical conventional treatment for Grade III and IV capsular contracture is removal of the implant, requiring additional surgery and potential for re-occurrence of the condition if the implants are replaced. However, as discussed in more detail below, it has been found that LLLT is beneficial in the treatment of Grade III capsular contracture and Grade IV capsular contracture.

Many alternatives to surgery have been trialed for capsular contracture including systemic treatment with fluoroquinolone to reduce or prevent scarring, and use of Leukotriene to reduce the effect of scarring. Other treatments, including ultrasound therapy, have also been trialed. However, none of the alternatives to surgery has been recognized as consistently effective and/or to have acceptable side-effects.

The emphasis has recently been on the prevention of capsular contracture through alternative implant surface techniques to reduce the potential for the fibers to stick or be attracted to the implant surface. The positioning of the implant in relation to muscle structure is also believed to have an impact and also intense adherence to infection control. Once again, a consistently effective technique has not been identified.

A pre-treatment of breast surgery patients with low level laser (visible red) has been used to reduce post surgical swelling and pain. Similarly, pre treatment with laser prior to breast augmentation surgery has been used and reports a post surgery pain reduction effect.

Given that LLLT increases fibroblast activity, it is conceivable that LLLT would be considered to have an unlikely positive effect on capsular contracture. The inventors hypothesize that the LLLT effect is possibly related to fluid movement, or a controlling mechanism that "turns off" the production of collagen, or a mechanism where the collagen fibers are released from their constricted form.

LLLT offers a non-invasive, minimal risk, low cost treatment option for capsular contracture. Several authors have concluded that LLLT reduces inflammation in the short term however studies also indicate that LLLT activates myofibroblast proliferation. Myofibroblasts are responsible for production of fibrous tissue which is contractile in nature, which is potentially positive for wound healing; however, myofibroblasts are responsible for production of fibrous tissue which is contractile in nature. The myofibroblasts (and fibrous tissue) are a negative when trying to reduce and/or stop capsular contracture and/or allowing capsular contracture to resolve. This is potentially why LLLT has not been used as a treatment for capsular contracture in the past. In the various embodiments of the present invention, the LLLT influences the inflammatory cascade by messaging tissue matrix structures to reduce or resolve the creation and/or maintenance of contractures.

In one embodiment illustrated in FIG. 1, a laser device 100 (e.g., a LTU904H (RianCorp Pty Ltd, Adelaide, Australia) laser device) emits LLLT for application of low power levels (e.g., less than about 1 Watt, between about 1 milliwatt and about 5 milliwatts, and, in an embodiment discussed below, between about 2.5 milliwatts and about 5 milliwatts) of near infra-red or red light (e.g., at a single wavelength between about 600 nm and about 1100 nm, at a single wavelength between about 600 nm and about 1000 nm, and at a single wavelength of about 900 nm) to a subject 102 (e.g., a mammalian subject) in a predetermined arrangement. For example, the laser 100 emits a 904 nm laser beam, while maintaining the safety classification of Class I (FDA CDRH) or Class 1M (EN 60825). The laser beam creates low level near-infrared radiation. The exemplary laser device 100 is capable of operating at wavelengths between about 600 nm and about 1100 nm. The low level radiation can be delivered to the subject 102 either directly or via optical transmission fiber. The exemplary laser device 100 is also capable of delivering a low level near infrared radiation having an average power range from about 1 micro-Watt to about 1 Watt, such that the device may be operated to apply a laser beam having an output power between approximately 1 mW and approximately 5 mW, or between approximately 2.5 mW and approximately 5 mW.

In one embodiment, a pulsed form of the laser beam is used. The pulsed form of the laser stimulates and alters the relevant cells as well as penetrates the skin of the patient to reach a relevant area of physiological concern (e.g., scar tissue 142 proximate to an implant 104 and/or the implant 104 itself). More specifically, the pulsed form of the laser beam creates the low level near infrared radiation in the scar tissue 142 and/or the implant 104. For example, the exemplary laser device 100 is operable to deliver a pulsed laser beam having a pulse width between about 100 nanoseconds and about 500 nanoseconds (e.g., about 200 nanoseconds), at a frequency between about 1000 Hz and about 5000 Hz (e.g., about 5000 Hz). The frequent, wide pulses of low level near infrared radiation laser energy are believed to produce a photochemical effect in the subject, inducing chemical changes in the cells of the subject. This effect can be contrasted with the high energy, infrequent and short pulse laser applications (e.g., produced by a Q-switched laser) that generate a shock wave to create an energy pulse, typically used for clinical applications requiring photodisruptive effects (e.g., shattering kidney stones or breaking the capsule associated with secondary cataracts).

In another embodiment, a non-pulsed laser beam (e.g., a continuous wave laser beam) may be used.

A Class I laser device has benefits to the clinician and patient in that the laser is deemed less likely to be harmful to humans relative to higher class lasers. Since Class I lasers are relatively less harmful, procedures and training are not as rigorous as if the laser had a higher classification. Furthermore, Class I laser devices (e.g., the exemplary laser device 100) are typically cheaper to purchase, maintain and/or replace. The laser device 100 is generally more reliable because the active device and the control electronics are relatively simpler and good design practice ensures a relatively higher Mean Time Between Failures.

In the embodiment illustrated in FIG. 1, the exemplary laser device 100 includes a unitary (e.g., one-piece) body 110. It is contemplated that a battery (not shown) is housed in the body 110. In that case, the body 110 also includes a socket 112 for accepting a battery charger connector and a battery charging indicator lamp 114. A laser producing component 116 produces a Class I laser beam of low power levels (< about 1 Watt) of near infra-red or red light (about 600 nm-about 1100 nm) and, as discussed in the embodiment below, has an output level (e.g., power) of between about 2.5 milliwatts and about 5 milliwatts.

The exemplary laser device 100 is also contemplated to include a treatment control switch 120. The treatment control switch 120 is contemplated to be a touch-sensitive switch, a pressureless switch, a slide switch, a membrane switch, or any other type of switch. A power switch 122 (e.g., an ON/OFF switch) is contemplated to be a touch-sensitive switch, a membrane switch, a pressureless switch, a slide switch, a membrane switch, or any other suitable type of switch. The power switch 122 may optionally include an indicator lamp 124.

An output level switch 126 controls a power output level of the laser device 100. In the illustrated example, is a HI/LO switch that may be set to either to the two (2) levels. For example, in one embodiment, when the output level switch 126 is set to a "High" output level, the laser device 100 may output about 5 milliwatts, and when the output level switch 126 is set to a "Low" output level, the laser device 100 may output about 1 milliwatt or about 2.5 milliwatts. The output level switch 126 optionally includes respective indicator lamps 130 for the respective settings. The output level switch 126 is contemplated to be a touch-sensitive switch, a pressureless switch, a slide switch, a membrane switch, or any other type of switch. In other embodiments, it is also contemplated that the switch is a continuous switch so that the power output level may be set to about 1 milliwatt, about 5 milliwatts, or any power output level therebetween. It is to be understood that both the Low and High power output levels (e.g., about 2.5 milliwatts to about 5 milliwatts) of the exemplary laser device may be considered low level output laser powers. Other embodiments are also contemplated having a Low output level as low as about 1 micro-Watt and a High output level as high as about 1 Watt. In any of the embodiments discussed above, it is contemplated that an output level switch is a continuous switch that can select any output level between the Low output level (e.g., about 1 micro-Watt) and the High output level (e.g., about 1 Watt).

A timer 132 may be provided for tracking an elapsed treatment time.

The exemplary laser device 100 also includes at least one label 134. For example, the label 134 may include a warning label, an instruction label, etc.

A probe 136 is positioned proximate to an end of the laser device 100. As illustrated, the probe 136 includes a transmission window 140. A laser beam produced by the laser producing component 116 exits the laser device 100 via the transmission window 140 of the probe 136 and may be directed to the subject 102. The probe 136 may be positioned proximate to the scar tissue 142 experiencing capsular contracture so that the laser beam may cause the low level near infrared radiation to be directed into at least one of the scar tissue 142 and the implant 104.

It is contemplated that the laser device 100 illustrated in FIG. 1 radiates a single beam having, for example, a diameter of about 6 mm and the exemplary output power levels described above. However, it is also contemplated to use a laser arrangement that includes multiple non-overlapping laser beams (e.g., spots) of, for example, substantially about 5 mm in diameter and spaced about 10 mm to about 20 mm apart. In one embodiment, each of the non-overlapping laser beams has substantially the same power level of, for example, somewhere between approximately 2.5 milliwatts and approximately 5 milliwatts. However, other embodiments are also contemplated in which one or more of the non-overlapping laser beams have different power levels.

Method

Figure 2:
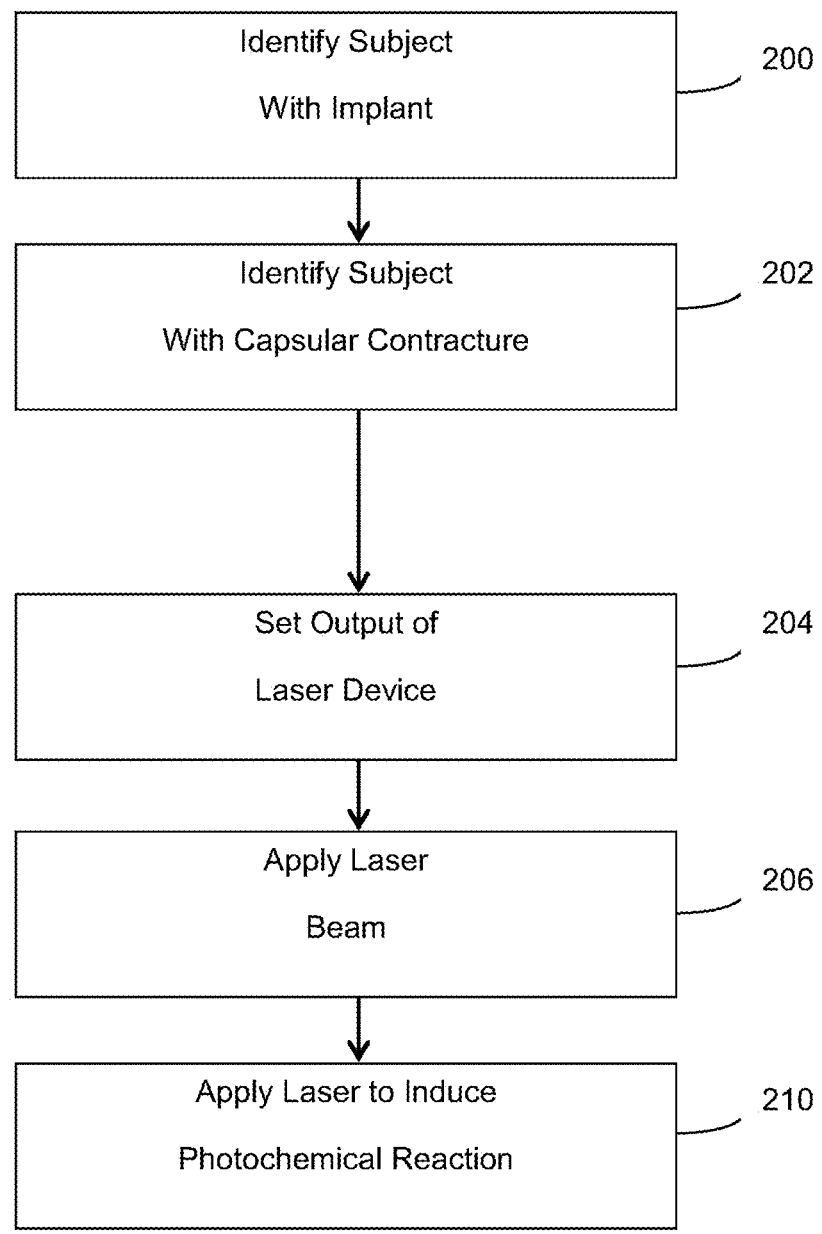
FIG. 2 is an exemplary methodology of treating capsular contracture in accordance with one embodiment illustrating principles of the present invention.

A method for reducing capsular contracture associated with tissue 142 (e.g., scar tissue) in a subject 102 is described with reference to FIGS. 1 and 2. With reference to FIG. 2, an exemplary methodology of the system shown in FIG. 1 for reducing capsular contracture is illustrated. As illustrated, the blocks represent functions, actions and/or events performed therein. It will be appreciated that electronic and software systems involve dynamic and flexible processes such that the illustrated blocks and described sequences can be performed in different sequences. It will also be appreciated by one of ordinary skill in the art that elements embodied as software may be implemented using various programming approaches such as machine language, procedural, object-oriented or artificial intelligence techniques. It will further be appreciated that, if desired and appropriate, some or all of the software can be embodied as part of a device's operating system.

With reference to FIGS. 1 and 2, a subject 102 having an implant 104 is identified in a Step 200. A subject 102 with the implant 104 and experiencing capsular contracture in, for example, the scar tissue 142 is identified in a Step 202.

Once the subject 102 with the implant 104 experiencing capsular contracture is identified, the output level of the laser device 100 is set in a Step 204. For example, the output level is set via the output level switch 126 to either the High output level or the Low output level. In one embodiment, the output level is set to ensure the low level near infrared radiation interacts with (e.g., reaches) at least one of the scar tissue 142 and the implant 104. Since near infrared wavelengths penetrate the skin of the subject 102 between about 15 mm to about 25 mm into the tissue, positioning the probe 136 proximate to the scar tissue 142 and/or the implant 104 is sufficient for ensuring the near infrared waves reach the scar tissue 142 and/or the implant 104. In addition, it has been found that there is a systemic effect to directing the near infrared waves of the laser beam to anywhere on the subject 102. Therefore, the near infrared radiation does not actually have to reach the fibrosis (i.e., the scar tissue 142 and/or the implant 104). For example, experimental work has shown that actually treating an armpit area of the subject 102 with the near infrared laser beam radiation will have an effect on capsular contracture in the breast area. However, a faster reaction will occur if the actual site (e.g., the breast area of the subject 102) is treated. A low level laser beam is applied in a Step 206 using, for example, the laser beam produced by the laser device 100. The laser beam creates low level near infrared radiation. Therefore, the low level near infrared radiation (e.g., the relatively low power output level of 5 milliwatts or less, such as between about 1 milliwatt and about 5 milliwatts) produced by the laser device 100 is used as a treatment for capsular contracture.

The low level near infrared radiation is applied in a Step 210 to induce a photochemical reaction at a cellular level in the scar tissue 142 proximate the implant 104. A photochemical reaction occurs when, for example, energy from the laser effects one or more molecular processes by inducing at least one biochemical reaction. The reactions may not be immediate. The laser may induce a cascade of reactions that finally lead to a physical change.

As discussed above, the low level near infrared radiation (e.g., about 5 milliwatts or less) applied to the scar tissue 142 and/or the implant 104 does not produce any substantial heat in the scar tissue 142. When laser energy is absorbed by tissue there are several potential recognized effects. One of the potential effects is a photochemical effect. Other potential tissue effects from laser energy include photothermal effects, where laser energy creates thermal effects (e.g., tissue denaturing), photomechanical effects, where the laser breaks molecular bonds (e.g., tattoo ink), etc. For example, in the present embodiment, even at the High output level, the laser device 100 will not produce any substantial heat in either the scar tissue 142 or the implant 104 if the low level infrared radiation (e.g., 5 milliwatts or less) is only applied to the scar tissue 142 and the implant 104 in a predetermined dose. In one example, the predetermined dose is about 1.5 joules per square centimeter ($J/cm^2$), although other doses are also contemplated, such as, for example doses between about 0.5 $J/cm^2$ and about 3 $J/cm^2$. A predetermined dose of about 1.5 $J/cm^2$ may be achieved, in one example, by delivering about 5 milliwatts for about 300 seconds, since 1 watt=1 joule/second. Other laser treatment durations may be used to achieve a desired energy dose, for example, between about 30 seconds and about 100 seconds per treatment point, with about 5 to about 30 points or locations being treated, depending on the average output power and desired energy dose selected.

Since no substantial heat is produced in either the scar tissue 142 or the implant 104, the effects achieved in the scar tissue 142 are not thermal related, but, instead, related to the photochemical reaction at a cellular level.

Investigation I

SUMMARY

An investigation was conducted to determine the effect and mechanism of action of low level infra-red laser on capsular contracture of breast implants in a mouse model. As noted above, capsular contracture occurs when connective tissue and associated cells "squeeze" the breast implant, thereby causing distortion and perceived hardening of the implant. Capsular contracture may be a major complication of breast reconstruction following breast cancer surgery/reconstruction. Currently, the treatment option for capsular contracture is surgical removal or replacement of the implants. LLLT has been clinically used for a variety of conditions, specifically post mastectomy lymphoedema, and is registered in the United States by the Food and Drug Administration (FDA) and in Australia by the Therapeutic Goods Administration (TGA).

The investigation followed an existing mouse model established for capsular contracture. Mice were implanted with a silicon gel implant under the skin on the back, and were then radiated with gamma radiation to the implant site to simulate breast cancer radiation treatment. Previous studies indicated that contracture would develop over 21 days and progress over 42 days. Animals were divided into five (5) groups and given either LLLT or placebo laser treatment (i.e., no LLLT treatment). The LLLT treatment was administered to two (2) of the groups for two (2) minutes and created no heat or physical sensation. The placebo laser treatment was administered to two (2) of the other three (3) groups, while the fifth group received no treatment.

Group A received the placebo laser treatment and Group B received the active laser LLLT immediately following implant surgery and additional weekly treatments for 3 weeks. These treatments were performed to determine if LLLT effects development of contracture.

Group C received the placebo laser treatment and Group D received the active laser LLLT commencing 21 days after surgical implant and additional weekly treatments for 2 weeks. These treatments were performed to determine if LLLT effects contracture once the contracture has developed.

Group E received were maintained without treatment, as controls for 42 days after inducement of capsular contracture.

The degree of contracture was assessed using pathology review of collected tissue samples and micro CT imaging. Micro CT imaging is a technique where a 3D microscopic image can be developed to allow for greater review of distortion of implants. The micro CT imaging technique has been described in the medical literature and is non-invasive.

The hypothesis was that LLLT would reduce capsular contracture and, therefore, provide a non-invasive treatment option for patients who have capsular contracture following reconstruction after breast cancer.

Details

Forty-five mice were obtained from, and maintained at, Flinders University School of Medicine Animal House under standard feed and water regimen. Animals were randomly assigned to one of the five (5) groups (n=7 per group):

Group A: Placebo laser treatment at Days 0, 7, and 14 following x-ray inducement of capsular contracture;

Group B: Active LLLT at Days 0, 7, and 14 immediately following x-ray inducement of capsular contracture;

Group C: Placebo laser treatment at Days 21, 28 and 35 after x-ray inducement of capsular contracture;

Group D: Active LLLT at 21 weeks after x-ray inducement of capsular contracture; and Group E: 5 animals maintained without treatment, as controls for 42 days after inducement of capsular contracture.

Groups A and B were maintained for 28 days with normal food and water.

Groups C, D, and E were maintained for 42 days with normal food and water.

Induction of Capsular Contracture: On Day 0, all 45 mice were surgically anesthetized and a 1 cm diameter saline "breast" implant was implanted under the skin on the back via a 1.0 cm transverse incision. The incision was closed with "tissue glue." While still under anesthesia, all 45 animals were subjected to 1 dose of 10 Gy gamma irradiation, delivered locally with lead shielding to avoid systemic effects.

Laser Irradiation: Two lasers (LTU-904 Riancorp Pty Ltd, Adelaide) were used. The LTU-904 laser is TGA registered for the treatment of muscular skeletal pain and post mastectomy treatment of lymphoedema, in humans and FDA registered for the treatment of post mastectomy lymphedema. The lasers used in this experiment were the same as the currently available unit, however, one laser was de-activated to produce no laser output (placebo treatment). The active laser operated at 904 nm (infrared, invisible) at a very low power level of 5 mW. No heating of tissue was created. The active laser produced no physical sensation in humans. The lasers (placebo or active) were directed at two locations over the implant site for one minute each (total 2 minutes).

Groups A and B: At 7, 14 and 21 days, Group a) and b) animals were lightly sedated using inhaled isoflurothane (2-4%) and received active or placebo laser treatment, as described above. Active or placebo laser treatment was delivered on a bench top. On Day 28, animals from Groups A and B were taken for Micro CT, lightly sedated using inhaled isoflurothane for the duration of Micro CT, and then euthanized using ip Lethobarb. The implant and associated tissue samples were collected from all animals.

Groups C and D: At days 21, 28 and 35, animals in Groups C and D were lightly sedated using inhaled isoflurothane (2-4%) and received active or sham laser treatment (as noted above) on a bench. At 42 days after surgery, animals from Groups C and D were transported for Micro CT, lightly sedated using inhaled isoflurothane for the duration of the CT Scan, and then euthanized using ip Lethobarb. The implant and associated tissue samples were collected from all animals.

Group E: After surgery and while still under anesthesia, Group E animals (total 5) were transported for MicroCT scans. The animals were gently restrained in a plastic tube to allow scanning for 20 minutes. Animals were subjected to 1.8 gy per scan. These animals were then returned.

Figure 5:
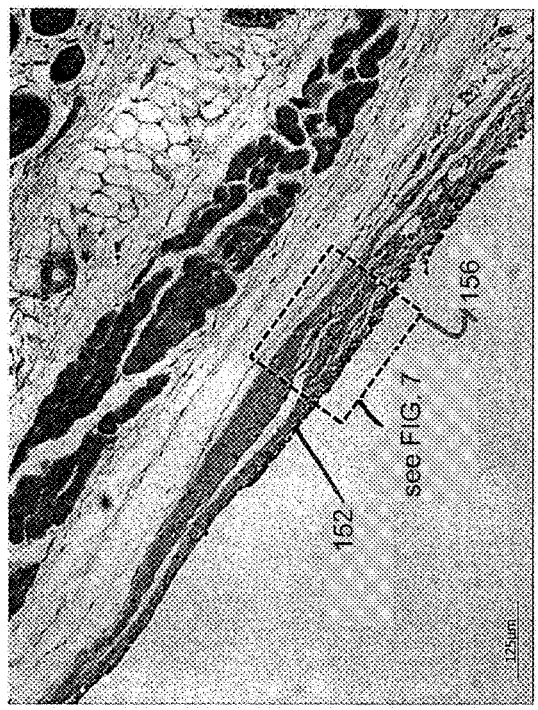
FIG. 5 illustrates a capsule surrounding an implant with no treatment by a laser.
Figure 4:
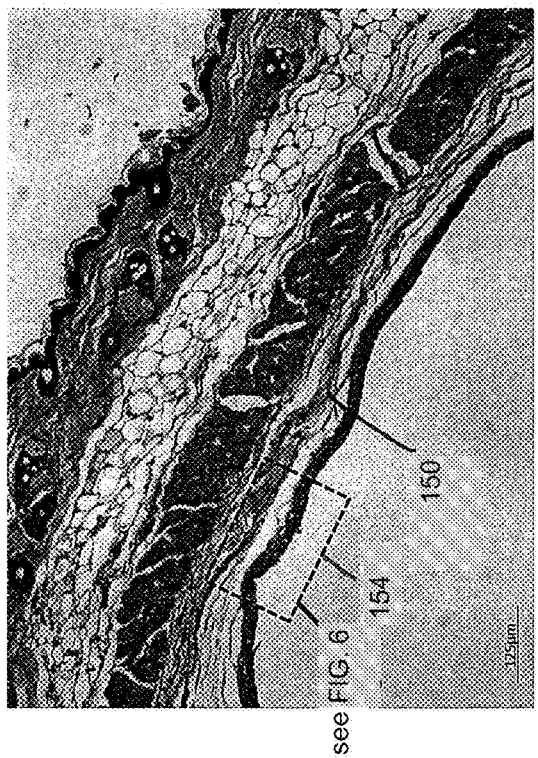
FIG. 4 illustrates a capsule surrounding an implant after treatment by a laser in accordance with one embodiment of the present invention.
Figure 7:
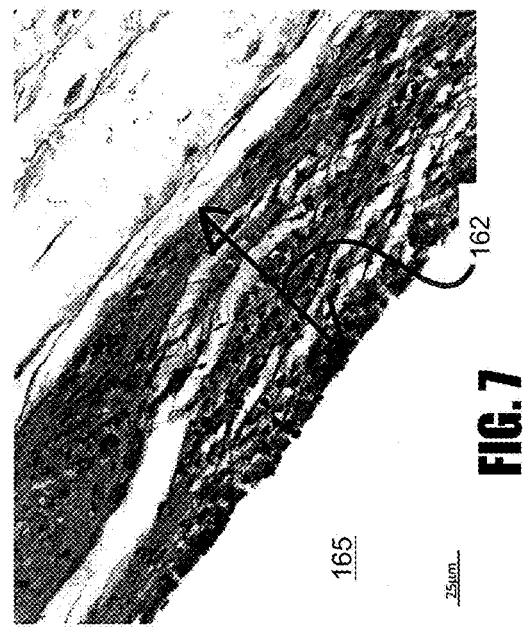
FIG. 7 illustrates an enlarged view of a section of the capsule of FIG. 5.
Figure 6:
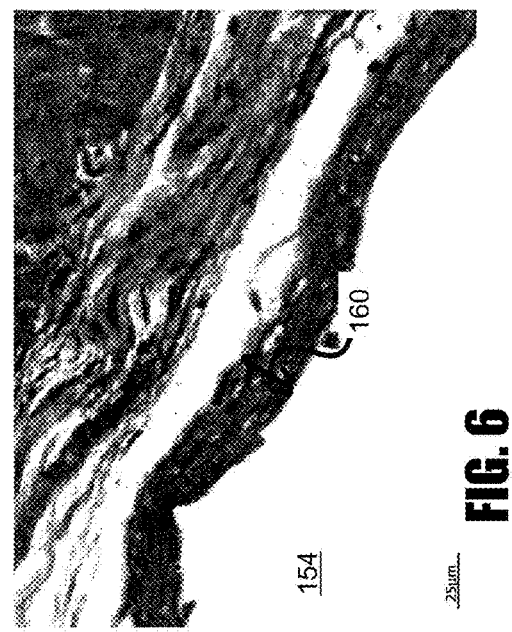
FIG. 6 illustrates an enlarged view of a section of the capsule of FIG. 4.

With reference to FIG. 3, implants 104 are shown in situ from 3D micro CT scanning. FIGS. 4 and 5 illustrate at least one of Grade III and Grade IV capsular contracture pathologies 150, 152 for laser A (FIG. 4) and laser B (FIG. 5), respectively. In this example, the laser A (FIG. 4) delivered near infra-red or red light (about 600 nm-about 1100 nm) at low power levels (< about 1 Watt and, in an embodiment discussed below, from about 2.5 milliwatts to about 5 milliwatts). The laser B (FIG. 5) was not operated. FIGS. 6 and 7 illustrate enlarged portions 154, 156 of the at least one of the Grade III and Grade IV capsular contracture pathologies 150, 152, respectively. It is clear that respective thicknesses 160, 162 of the at least one of the Grade III and Grade IV capsular contracture pathologies 150, 152, respectively, are different. More specifically, the thickness 160 of the at least one of the Grade III and Grade IV capsular contracture pathology 150 treated with the laser A is less than the thickness 162 of the at least one of the Grade III and Grade IV capsular contracture pathology 152 treated with the laser B. Further, FIGS. 4 and 6 show that the capsules surrounding implants receiving LILT treatment were better organized histologically, with tight connective tissue layers parallel to the capsule surface, well-aligned fibroblasts, and moderate inflammatory cell infiltrate. In contrast, FIGS. 5 and 7 show that capsules surrounding implants receiving placebo treatment were less well organized, with more random connective tissue and fibroblast cell orientation, a greater degree of interstitial space and more inflammatory cell infiltrate. The more organized capsular structure evident in the capsules of the LLLT-treated implants is believed to be relevant in the efficacy of LLLT in reducing or preventing capsule contracture.

Investigation II

In another investigation, a LTU-904 laser (FDA approved for treatment of lymphadema) was used on 23 human patients with Grades III and IV capsular contractures. Patients underwent a total of six treatments. Each treatment lasted for 10 minutes, with treatments performed each week, and then a follow up was conducted at 4 weeks. After all of the treatments, twenty of the patients were asked the following questions:

Is your breast more comfortable since the laser treatment? If so, by what percentage is comfort improved?

Do you feel your breast is softer since the treatment? If so, by what percentage is it softer?

Is your breast improved enough that you will not undergo further surgery?

Would you have the laser treatment again to try and soften the breast further?

FIG. 8 includes a chart of the respective responses from the twenty interviewed patients.

Eight (8) of the 23 patients had had previous radiation. Surgical intervention was avoided in 91.3% of patients with at least one of Grade III and Grade IV capsular contraction. Of the patients who avoided surgery, the laser improved the stiffness of the breast by 10-95% with an average of 50.2%. The overall improvement in comfort for these patients ranged from 10-95% with an average of 52.1%.

Based on this investigation, it was found that LLLT is a promising alternative treatment for treating Grade III and Grade IV capsular contracture. In the majority of cases, both patients and surgeon observed significant tissue softening and improved breast contour after treatment with LLLT.

Although the embodiments of the present invention discussed above have described capsular contracture with breast implants, it is to be understood that capsular contracture may occur with any type of implants. In addition, the embodiments of the present invention discussed above may also be used for reducing capsular contracture with dental implants that have capsular fibrosis, intra-ocular lenses with excessive fibrosis, lap bands with excessive fibrotic contracture, and/or cochlear hearing implants with excessive fibrotic contracture. Obviously, other implants not mentioned here are also contemplated.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Parameters identified as "approximate" or "about" a specified value are intended to include both the specified value and values within 10% of the specified value, unless expressly stated otherwise. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

What is claimed is:

1. A method for treating one of Grade III capsular contracture or Grade IV capsular contracture in a mammalian subject, the method comprising:
    positioning a laser device proximate the subject having the Grade III capsular contracture or Grade IV capsular contracture; and
    applying, with the laser device, a low level laser beam having a wavelength between approximately 600 nm and approximately 1,000 nm toward an area of tissue of the subject having the Grade III capsular contracture or Grade IV capsular contracture to induce a photochemical reaction at a cellular level in the Grade III capsular contracture or Grade IV capsular contracture, including applying the laser beam to a plurality of locations on the subject, for a time period between approximately 30 seconds and approximately 100 seconds for each of the plurality of locations.

2. The method of claim 1, wherein the step of applying the laser beam comprises applying a pulsed laser beam having a pulse width between approximately 100 nanoseconds and approximately 500 nanoseconds.

3. The method of claim 1, wherein the step of applying the laser beam comprises applying a pulsed laser beam having a frequency between approximately 1000 Hz and approximately 5000 Hz.

4. The method of claim 1, wherein the step of applying the laser beam comprises applying a plurality of laser beams to the subject in a non-overlapping pattern.

5. The method of claim 4, wherein each of the laser beams has substantially the same power level.

6. The method of claim 4, wherein one or more of the laser beams have different power levels relative to each other.

7. The method of claim 4, wherein the step of applying the plurality of laser beams to the subject in the nonoverlapping pattern comprises applying the plurality of laser beams such that each of the plurality of laser beams is about 5 mm in diameter and is separated from the others of the plurality of laser beams by about 10 mm to about 20 mm.

8. The method of claim 1, wherein the step of applying the laser beam includes applying the laser beam to between five and thirty locations on the subject.

9. The method of claim 1, wherein the step of applying the laser beam comprises applying a pulsed laser beam.

10. The method of claim 1, wherein the step of applying the laser beam comprises applying a non-pulsed laser beam.

11. The method of claim 1, wherein the step of applying the laser beam includes applying a dose of low level near infrared radiation energy having an average output power between approximately 1 milliwatt and approximately 5 milliwatts.

12. The method of claim 1, wherein the step of applying the laser beam includes applying a dose of low level near infrared radiation energy having an average output power between approximately 2.5 milliwatts and approximately 5 milliwatts.

13. The method of claim 1, wherein the step of applying the laser beam includes applying a dose of low level near infrared radiation energy density of between approximately 0.5 joules per square centimetre and approximately 3 joules per square centimetre.

14. A method for treating contracture in a cochlear area in a mammalian subject, the method comprising:
    positioning a laser device proximate the subject having the contracture; and
    applying, with the laser device, a low level laser beam having a wavelength between approximately 600 nm and approximately 1,000 nm toward the cochlear area of the subject to induce a photochemical reaction at a cellular level in the contracture, including applying the laser beam to a plurality of locations on the subject, for a time period between approximately 30 seconds and approximately 100 seconds for each of the plurality of locations.

* * * * *